(12) United States Patent
Selover

(10) Patent No.: US 7,909,834 B2
(45) Date of Patent: Mar. 22, 2011

(54) SELF RETAINING SET SCREW INSERTER

(75) Inventor: Sean Selover, Tiverton, RI (US)

(73) Assignee: DePuy Spine, Inc., Raynham, MA (US)

( * ) Notice: Subject to any disclaimer, the term of this patent is extended or adjusted under 35 U.S.C. 154(b) by 854 days.

(21) Appl. No.: 11/014,389

(22) Filed: Dec. 15, 2004

(65) Prior Publication Data

US 2006/0149291 A1 Jul. 6, 2006

(51) Int. Cl.
*A61B 17/58* (2006.01)

(52) U.S. Cl. ......................................... 606/104

(58) Field of Classification Search ............ 606/61, 606/104, 99, 86 R, 86 A; 81/442–445, 453
See application file for complete search history.

(56) References Cited

U.S. PATENT DOCUMENTS

| | | |
|---|---|---|
| 1,592,987 A | 7/1926 | Mayer |
| 2,370,407 A * | 2/1945 | McCartney .................. 81/453 |
| 2,506,922 A | 5/1950 | Hansen |
| 2,729,998 A | 1/1956 | Deliso |
| 2,775,913 A | 1/1957 | Deliso |
| 3,604,487 A | 9/1971 | Gilbert |
| 3,894,450 A | 7/1975 | Hill et al. |
| 5,095,779 A * | 3/1992 | Batten ............................ 81/55 |
| 5,139,499 A | 8/1992 | Small et al. |
| 5,308,357 A * | 5/1994 | Lichtman ..................... 606/205 |
| 6,183,472 B1 * | 2/2001 | Lutz ............................... 606/61 |
| 6,286,401 B1 * | 9/2001 | Hajianpour .................... 81/453 |
| 2004/0158258 A1* | 8/2004 | Bonati et al. ................. 606/104 |
| 2004/0255418 A1* | 12/2004 | Minkler et al. ............. 15/210.1 |
| 2005/0228400 A1* | 10/2005 | Chao et al. ................... 606/104 |

* cited by examiner

*Primary Examiner* — Eduardo C Robert
*Assistant Examiner* — Tara R Carter
(74) *Attorney, Agent, or Firm* — Nelson Mullins Riley & Scarborough LLP; Kevin J. Canning

(57) ABSTRACT

A self retaining screw inserter for inserting, positioning and removing a set screw of a spinal fixation system, includes an active reverse-collet retainer. The active reverse-collet retainer has fingers configured to move outward to engage and retain a set screw. When engaged, the fingers flare outward to engage the set screw.

14 Claims, 11 Drawing Sheets

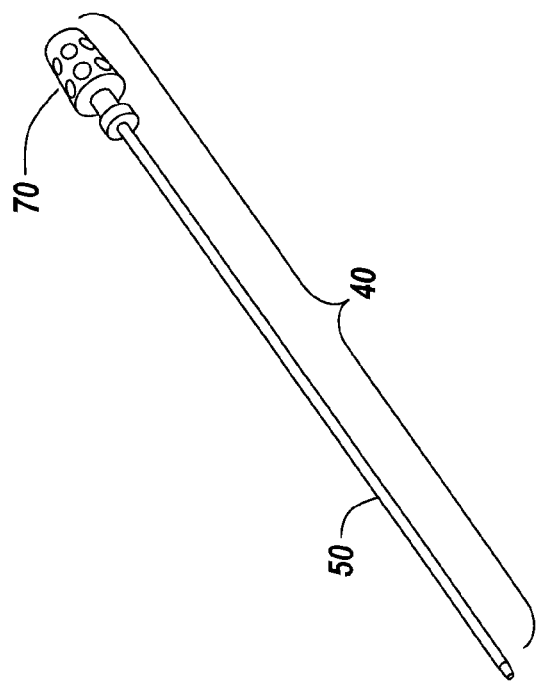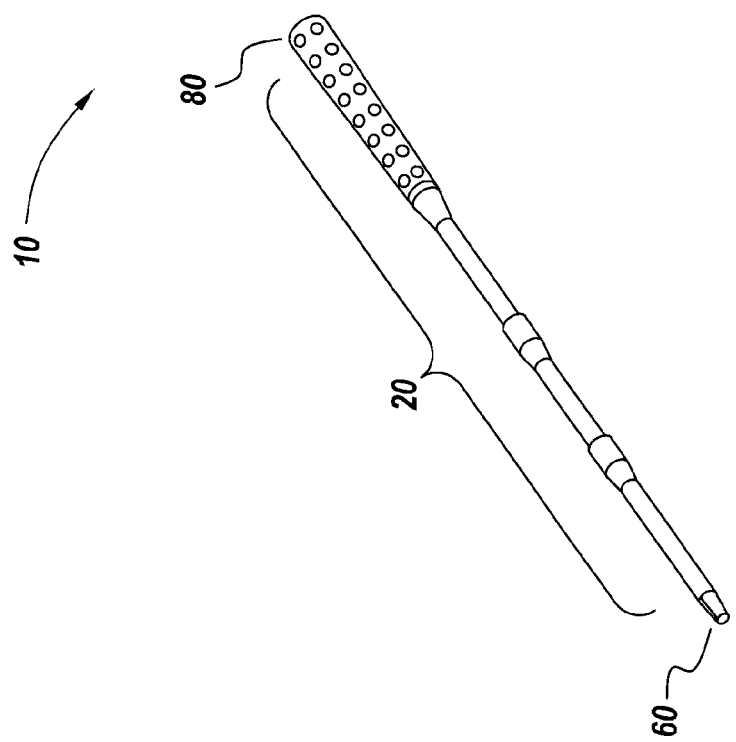
Fig. 1

SELF RETAINING SET SCREW INSERTER

FIELD OF THE INVENTION

The present invention relates to spinal fixation devices used in orthopedic surgery. More particularly, the present invention relates to an instrument for inserting and adjusting a spinal implant, such as a set screw.

BACKGROUND OF THE INVENTION

Spinal fixation systems may be used in orthopedic surgery to align, stabilize and/or fix a desired relationship between adjacent vertebral bodies. Such systems typically include a spinal fixation element, such as a relatively rigid fixation rod or plate, that is coupled to adjacent vertebrae by attaching the element to various anchoring devices, such as hooks, bolts, wires or screws. The spinal fixation element can have a predetermined contour that has been designed according to the properties of the target implantation site and, once installed, the spinal fixation element holds the vertebrae in a desired spatial relationship, either until desired healing or spinal fusion has occurred, or for some longer period of time.

Spinal fixation elements can be anchored to specific portions of the vertebra. Since each vertebra varies in shape and size, a variety of anchoring devices have been developed to facilitate engagement of a particular portion of the bone. Pedicle screw assemblies, for example, have a shape and size that is configured to engage pedicle bone. Such screws typically include a threaded shank that is adapted to be threaded into a vertebra, and a head portion having a spinal fixation element receiving element, which, in spinal rod applications, is usually in the form of a U-shaped slit formed in the head for receiving the rod. In many pedicle screws, the head is movable and preferably pivotable in all directions, relative to the shaft. The ability to move the head relative to the anchoring portion of the screw facilitates alignment and seating of a rod connecting a plurality of screws A set-screw, plug, cap or similar type of closure mechanism is used to lock the rod into the rod-receiving portion of the pedicle screw. In use, the shank portion of each screw is then threaded into a vertebra, and once properly positioned, a fixation rod is seated through the rod-receiving portion of each screw and the rod is locked in place by tightening a cap or similar type of closure mechanism to securely interconnect each screw and the fixation rod. Other anchoring devices include hooks and other types of bone screws Set screws are typically set into location using self-retaining screw inserters or self retaining drivers. These generally use small springs to retain the set screw on the end of the inserter or driver. These springs can deform or break when the inserter or driver experiences too much torque during insertion. Even though the inserter is just for initial insertion of a set screw, frequently surgeons over-torque the inserter causing premature failures. Another type of inserter uses a morse taper. These also are subject to wear and failure when overtorqued. Thus what is needed is a self-retaining screw inserter that does not rely on springs or morse tapers.

SUMMARY OF THE INVENTION

The present invention provides an instrument for inserting and adjusting a set screw that is capable of retaining a set screw on the end of the instrument. With the set screw retained on the end of the instrument, the set screw may be inserted in a percutaneous fashion to capture a spinal fixation element in a mating bone anchor. The present invention is intended to survive excessive torques, which can be applied during the insertion of a set screw, without the failing or lessening of the retaining capabilities of the instrument.

In accordance with a first aspect a self-retaining screw inserter comprises an active reverse-collet retainer. The reverse-collet retainer is active in that a user selects when the reverse-collet retainer will be engaged to retain a set screw. Likewise, a user may select to disengage the reverse-collet retainer thereby releasing a set screw.

In accordance with another aspect, a self-retaining screw inserter comprises an outer shaft defining an axially extending passageway and an inner shaft. The outer shaft comprises a distal tip comprising at least two fingers configured to retain a set screw, and a proximal end configured to receive an inner shaft. The inner shaft comprises a push rod configured to be inserted into the proximal end of the outer shaft and engage the distal tip of the outer shaft, wherein when the push rod engages the distal tip, the two or more fingers of the distal tip are moved or flared radially outward allowing the distal tip to retain a set screw.

In accordance with another aspect, a method of using a self retaining screw inserter comprising an outer shaft defining an axially extending passageway, the outer shaft comprising a distal tip comprising at least two fingers configured to retain a set screw, and a proximal end configured to receive an inner shaft; and an inner shaft comprising a push rod configured to be inserted into the proximal end of the outer shaft and engage the distal tip of the outer shaft; wherein when the push rod engages the distal tip, the two or more fingers of the distal tip are moved radially outward allowing the distal tip to retain a set screw, comprises the steps of placing a set screw on the distal tip of the outer shaft; and retaining the set screw by engaging the distal tip of the outer shaft with the push rod of the inner shaft, wherein the two or more fingers of the distal head are moved radially outward to engage the set screw In accordance with another aspect, a self-retaining screw inserter comprises an outer shaft defining an axially extending passageway and an inner shaft. The outer shaft comprises a distal tip comprising at least two fingers configured to retain a set screw, and a proximal end configured to receive an inner shaft. The inner shaft comprises a push rod configured to be inserted into the proximal end of the outer shaft and engage the distal tip of the outer shaft, and a knob on the proximal end of the push rod, wherein when the push rod engages the distal tip, the two or more fingers of the distal tip are moved radially outward by the push rod allowing the distal tip to retain a set screw.

In accordance with another aspect, a method of using a self retaining screw inserter comprising an outer shaft defining an axially extending passageway, the outer shaft comprising: a distal tip comprising at least two fingers configured to retain a set screw, and a proximal end having internal threads configured to receive an inner shaft; and an inner shaft comprising a push rod configured to be inserted into the proximal end of the outer shaft and engage the distal tip of the outer shaft, and a knob on the proximal end of the push rod having threads configured to engage the inner threads of the proximal end of the outer shaft, wherein when the thread of the knob of the inner shaft engage the threads of the proximal end of the outer shaft, the push rod engages the distal tip and the two or more fingers of the distal tip are moved radially outward by the push rod allowing the distal tip to retain a set screw; comprises the steps of placing a set screw on the distal tip of the outer shaft; and retaining the set screw by engaging the inner thread of the proximal end of the outers shaft with the threads of the knob of the inner shaft wherein the distal tip of the outer shaft is engaged by the push rod of the inner shaft and the two or more fingers of the distal head are moved radially outward to engage the set screw

BRIEF DESCRIPTION OF THE FIGURES

FIG. 1 is an exploded view of a self-retaining screw inserter according to an embodiment of the invention.

DETAILED DESCRIPTION OF THE INVENTION

Figure 2:
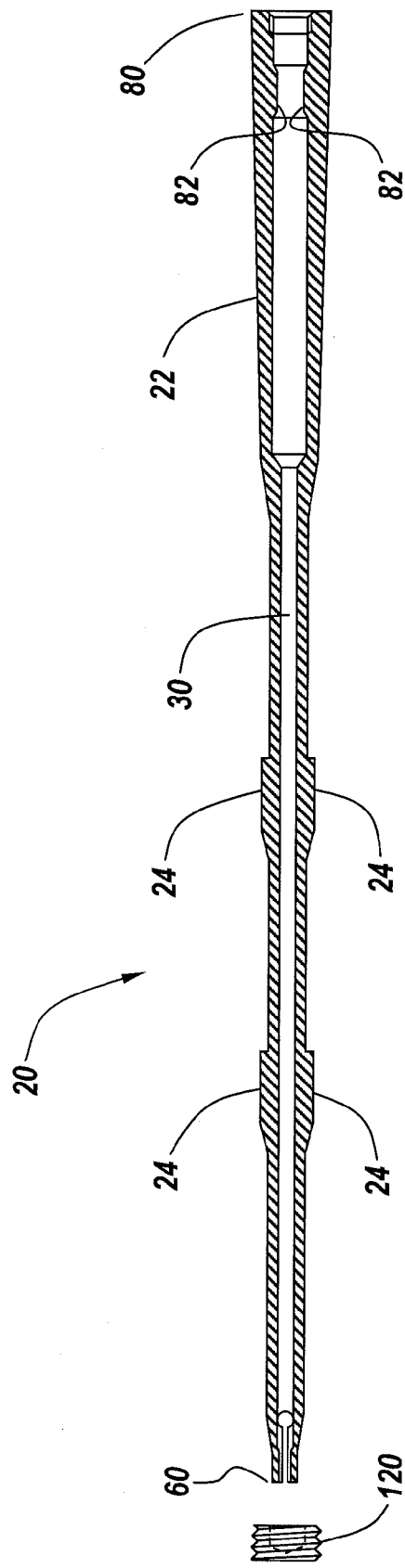
FIG. 2 is a cross-sectional side view of the outer shaft of the self-retaining screw inserter of FIG. 1.

The present invention will be described below relative to an illustrative embodiment. Those skilled in the art will appreciate that the present invention may be implemented in a number of different applications and embodiments and is not specifically limited in its application to the particular embodiments depicted herein.

The present invention provides an improved self-retaining set screw inserter for the insertion and removal of set screws used in a spinal fixation system. The active, secure, and durable retention provided by the present invention allows for the use of the inserter percutaneously.

The self-retaining screw inserter of the present invention features an active reverse-collet retainer. Using this reverse-collet retainer, a user, such as a surgeon may actively retain or release set screws for positioning purposes. Preferably, the reverse-collet retainer has at least two fingers configured to move radially outward to retain a set screw placed on the retainer when the retainer is engaged. The reverse-collet-retainer is usually attached on the end of a shaft for insertion into a body. In certain embodiments a user may be able to engage or disengage the retainer from the end of the shaft opposite the retainer. The configuration and operation of the self-retaining screw inserter may be better understood from the following figures and descriptions.

FIG. 1 is an exploded view of one embodiment of a self-retaining screw inserter 100 for percutaneous placement of set screws. The screw inserter 10 comprises an outer shaft 20 and an inner shaft 40. The outer shaft 20 defines an axially extending passageway. The outer shaft 20 comprises a distal tip 60 and a proximal end 80. The inner shaft comprises a push rod 50 configured to be inserted into the proximal end 80 of the outer shaft 20 and engage the distal tip 60 of the outer shaft 20. In certain embodiments the inner shaft 40 further comprises a knob 70 on the proximal end of the push rod 50 providing additional control of the screw inserter.

FIG. 2 depicts a cross-sectional side view of the outer shaft 20. The outer shaft 20 defines an axially extending passageway 30 configured to receive the inner shaft. The outer shaft has a distal tip 60 and a proximal end 80. The proximal end 80 is configured to receive the inner shaft. The push rod of the inner shaft is inserted into the passageway 30 through the proximal end 80. In certain embodiments, the proximal end 80 has threads 82 on the inner surface of the passageway 30 configured to mate with threads on the inner shaft.

The outer shaft 20 is preferably made of stainless steel or other surgical grade materials. In certain embodiments, the outer shaft 20 has surface features on the outer surface to assist in manipulation of the screw inserter. For example, portions of the outer surface may be provided with grips 22. In some embodiments, the outer shaft 20 has scallops 24 on the outer surface to reduce pressure build up when inserting or removing the screw inserter percutaneously. Other embodiments will be apparent to one skilled in the art given the benefit of this disclosure.

Figure 3:
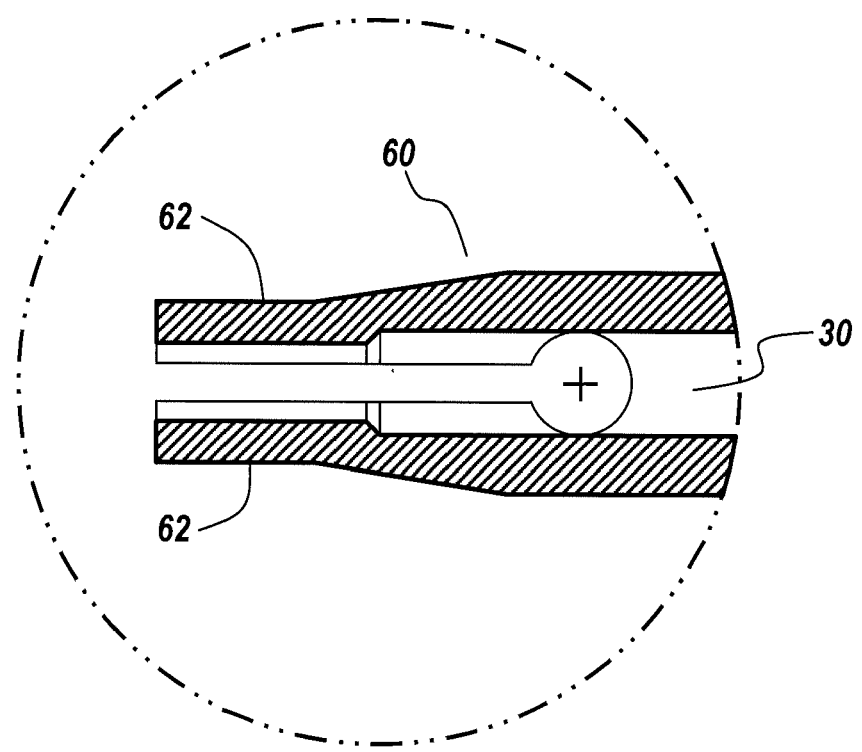
FIG. 3 is a close-up cut-away view of the distal tip of the outer shaft of FIG. 2.
Figure 3A:
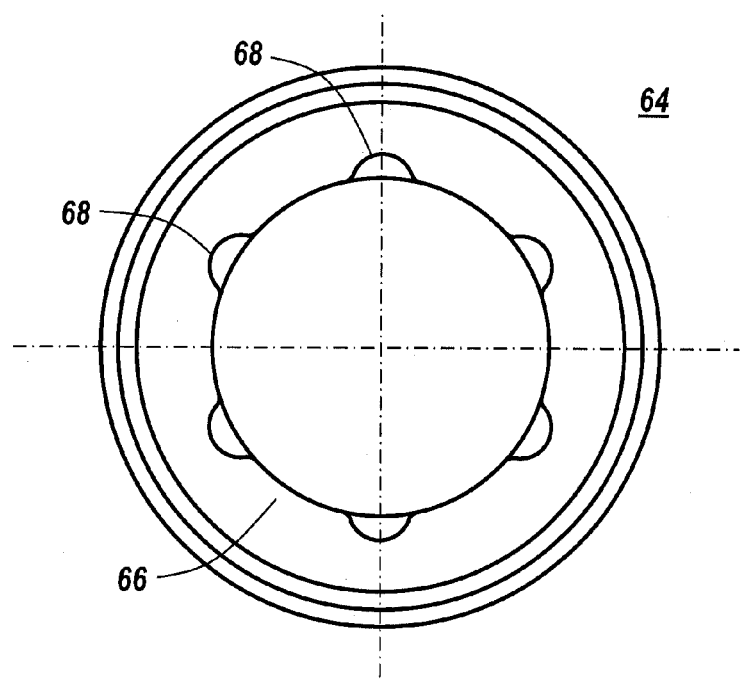
FIG. 3A is a head-on view of a modified Torx head configuration for the distal tip of FIG. 3.

FIG. 3 is a close-up cut-away view of one embodiment of a distal tip 60 of the outer shaft 20. In this embodiment, the distal tip is functioning as a reverse-collet retainer of the screw inserter. The distal tip 60 comprises at least two fingers 62. In certain embodiments there may be more than two fingers 62. The fingers 62 of distal tip 60 are shaped so as to engage a set screw. Examples of suitable shapes include, but are not limited to, Torx head, modified Torx head, hex head, Philips head, or the like. An example of a modified Torx head 64 can be seen in FIG. 3A. The modified Torx head 64 features a cylinder 66 with six lobes 68 equally spaced around the diameter of the cylinder 66. Other implementation will be apparent to one skilled in the art given the benefit of this disclosure.

Figure 3B:
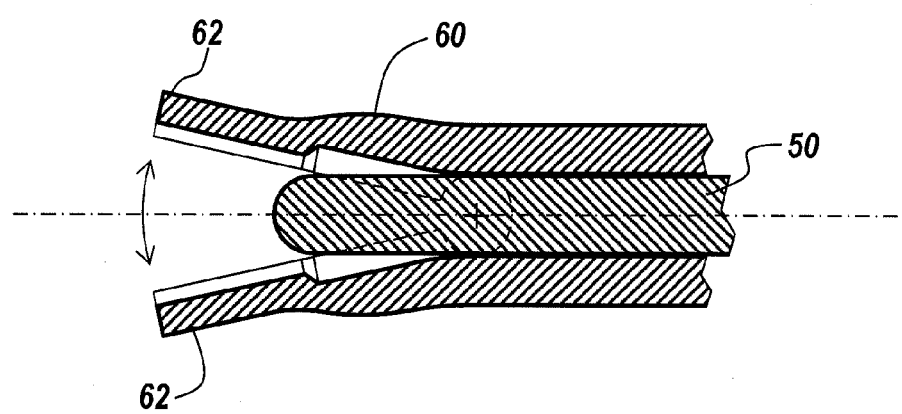
FIG. 3B is a close-up cut away view of distal tip of FIG. 3 in an engaged state.

Referring now to FIG. 3B, the distal tip 60 is configured such that when the push rod 50 of the inner shaft 40 is inserted into the passageway 30 of the outer shaft 20 the push rod 50 engages the distal tip 60. The distal tip 60 is smaller in diameter than the rest of the outer shaft 20 so when the push rod 50 engages the distal tip 60, the fingers 62 are moved or flared radially outward allowing the fingers 62 to engage a set screw 120.

Figure 4:
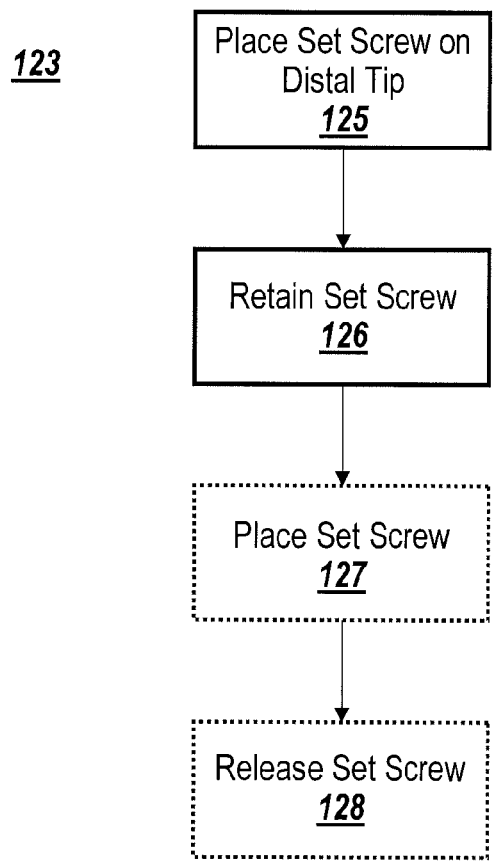
FIG. 4 is a block diagram flow chart of a method of using the self-retaining screw inserter of FIG. 1

A flow chart 123 depicting one embodiment of the process of using the self-retaining screw inserter of the present invention can be seen in FIG. 4. The first step 125 is placing a set screw on the distal tip 60 of outer shaft 20. The next step 126 is retaining the set screw by engaging the distal tip 60 with the push rod 50 of the inner shaft 40. This causes the fingers 62 of the distal tip 60 to move or extend radially outward and engage the set screw thereby securing the set screw 120 on the distal tip 60. Optionally, the set screw may then be placed in a desired location, step 127. In optional step 128, the set screw may then be released from the distal tip 60 by disengaging the push rod 50 from the distal tip 60 wherein the fingers 62 move or retract radial inward disengaging the set screw. Using this method set screws may be both inserted and removed percutaneously. Other uses or implementations will be apparent to ones skilled in the art given the benefit of this disclosure.

Figure 5:
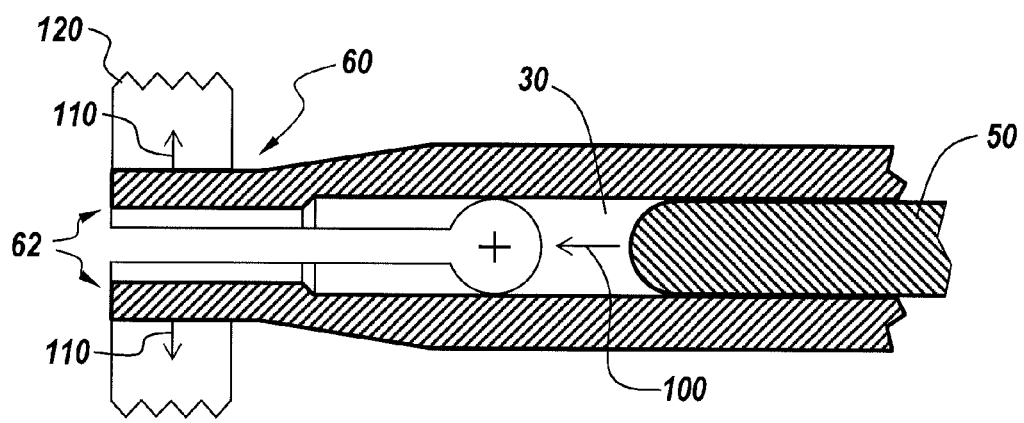
FIG. 5 is a cross-sectional side view depicting the operation of the self-retaining screw inserter of FIG. 1.

An example of the operation of one embodiment can be seen in FIG. 5. As shown here, the push rod 50 of the inner shaft travels down the passageway 30 toward the distal tip 60 in the direction indicated by arrow 100. The circumference of the outer shaft 20 decreases at the distal tip 60, so when the end of the push rod 50 engages the distal tip 60, the push rod moves or flares the fingers 62 of the distal tip 60 radially outward. The fingers 62 move radially outward as indicated by arrows 110 and engage the set screw 120 placed on the distal tip 60. The set screw 120 is thus retained on the distal tip 60 allowing a user to insert the set screw 120 percutaneously into the proper location without the fear of losing the set screw 120. The active interference used to secure the set screw 120 in this manner is more durable and resistant to torque forces that may be applied by a user on the screw inserter.

Inversely, once the set screw 120 is in a desired position, the set screw 100 may be released from the distal tip 60 by disengaging the push rod 50 from the distal tip 60. Here, the push rod 50 travels thru the passageway 30 in the direction opposite of arrow 100. Once the push rod 50 disengages from the distal tip 60, the fingers 62 move or retract radially inward in the direction opposite arrows 110 thereby disengaging the set screw 120.

Figure 6:
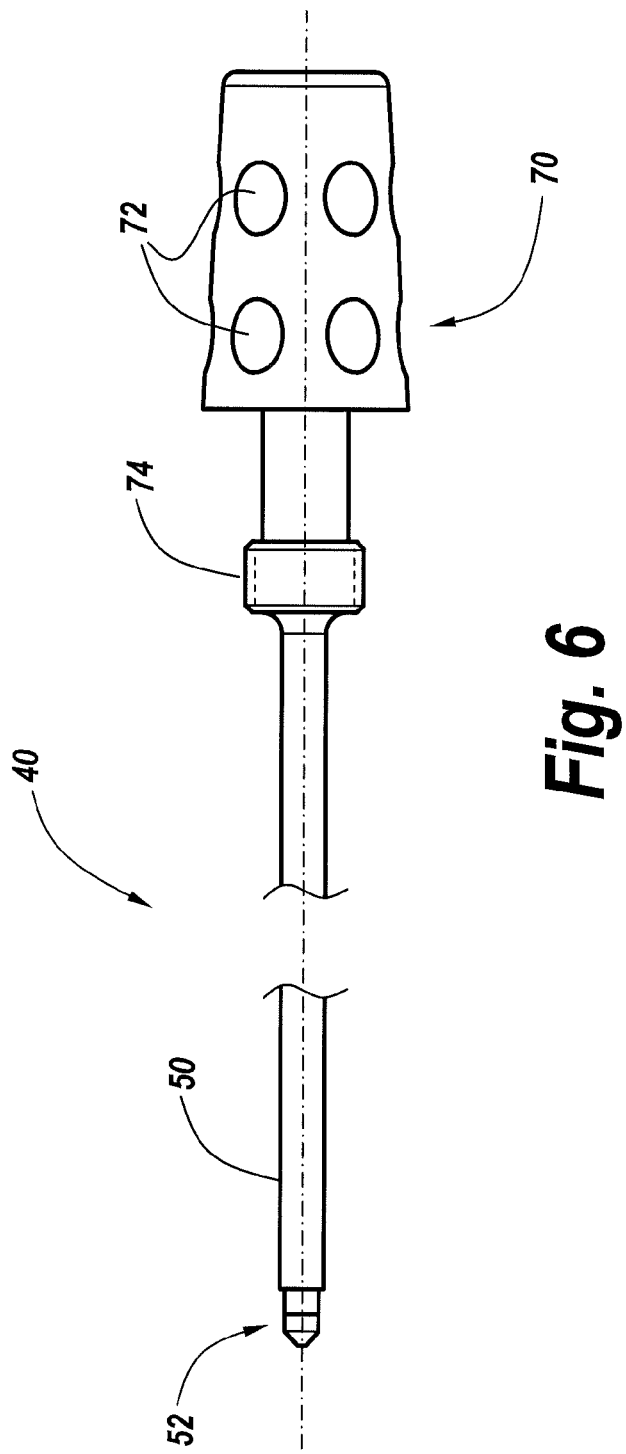
FIG. 6 is a close-up truncated view of the inner shaft of the self-retaining screw inserter of FIG. 1.

FIG. 6 is a close-up truncated view of one embodiment of an inner shaft 40. In this embodiment the inner shaft 40 features a push rod 50 and a knob 70. The push rod 50 is of the size and shape to slide along the passage way 30 of the outer shaft 20 so as to engage the distal tip 60 of the outer shaft 20. In certain embodiments, the tip 52 of the push rod is rounded so as to assist in the moving or flaring of the fingers 62 of the distal tip 60. The knob 70 is located on the proximal end of the push rod 50 opposite of the tip 52 of the push rod 50. The knob is preferably of a diameter greater than the diameter of the rest of the inner shaft 40 and may have surface configurations to assist in the manipulation of the inner shaft 40. Preferably, the inner shaft is made out of stainless steel or some other surgical grade material. Other implementations will be apparent to one skilled in the art given the benefit of this disclosure.

In certain embodiments, the inner shaft has threads 74 at the base of the knob at the proximal end of the push rod 50 configured to mate with threads 82 on the inner surface of the passageway 30 located at the proximal end 80 of the outer shaft 20. The threads 82 on the inner surface of the passageway 30 and the threads 74 at the base of the knob 70 allows the inner shaft 40 to be screwed into the outer shaft 20. In such embodiments, the greater diameter of the knob 70 provides a mechanical advantage when screwing or unscrewing the inner shaft 40.

Figure 7:
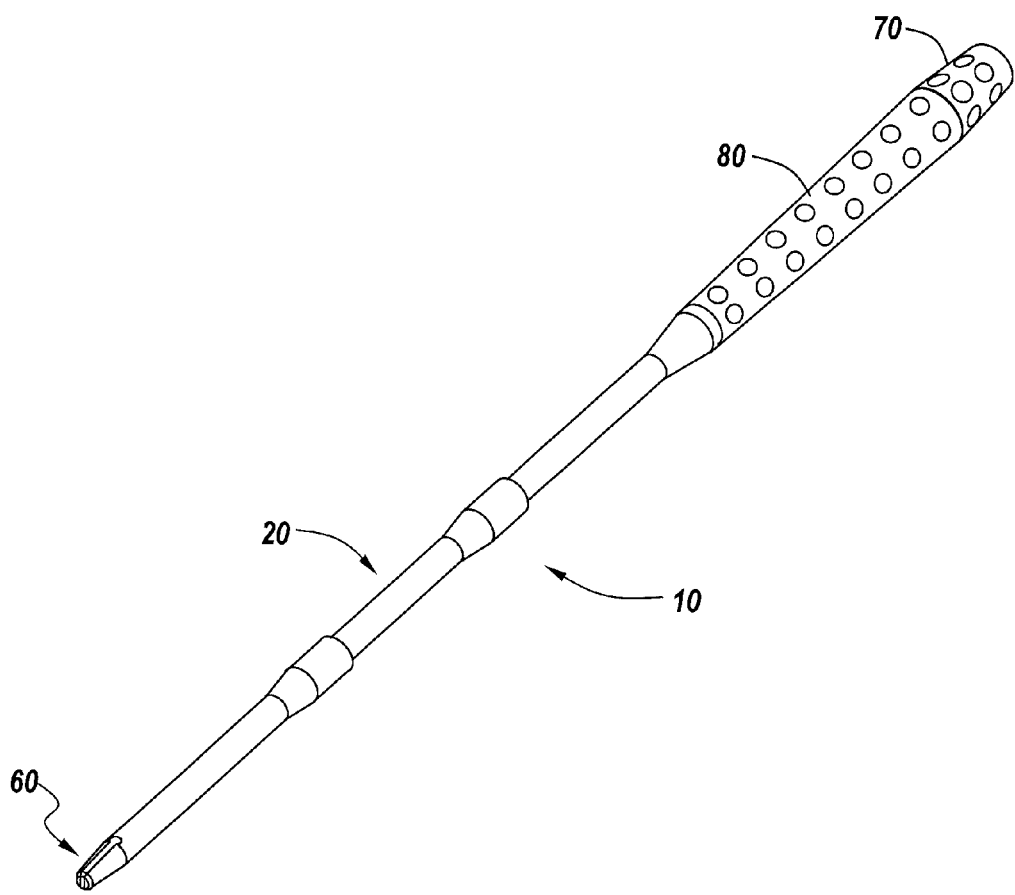
FIG. 7 is an assembled perspective view of a self-retaining screw inserter according to another embodiment of the invention.

FIG. 7 is a perspective view of one embodiment of a self-retaining screw inserter 10 wherein the inner shaft 40 has been screwed into the outer shaft 20. In this particular configuration, the screwing and unscrewing of the inner shaft 40 also controls the engaging and disengaging of the distal tip 60 by the push rod 50 and thus the retention and release of a set screw 120. This functionality can be seen in more detail in FIG. 8.

Figure 8:
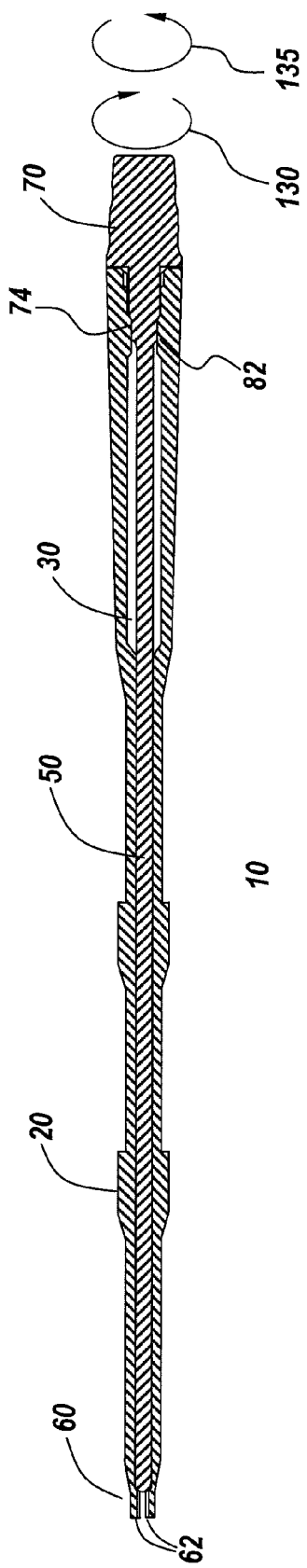
FIG. 8 is a cross-sectional side view of the self-retaining screw inserter of FIG. 7.

FIG. 8 is a cross sectional view of one embodiment of the self-retaining screw inserter 10 wherein the inner shaft 40 is screwed into the outer shaft 20. Here the push rod 50 is inserted into the passageway 30 so as to be able to engage the distal tip 60 of the outer shaft 20. The mating threads 74 and 82 control the depth of insertion of the push rod 50. In this embodiment, the threads 74 and 82 are configured so that turning the knob 70 clockwise, as indicated by arrow 130, screws in the inner shaft 40 (not shown in Figures) so that the push rod 50 engages the distal tip 60 to secure or retain a set screw 120. Turning the knob counter-clockwise, as indicated by arrow 135, disengages the push rod 50 from the distal tip 60.

Figure 9:
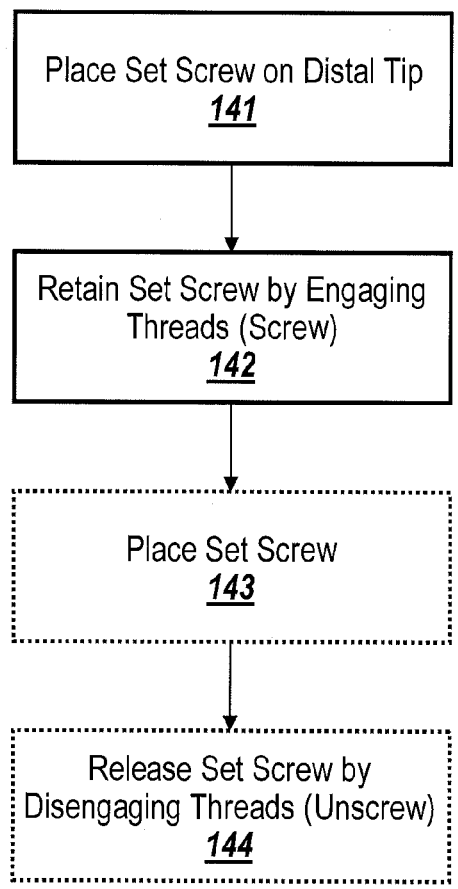
FIG. 9 is a block diagram flow chart of a method of using the self-retaining screw inserter of FIG. 7.

FIG. 9 is a flow chart 140 depicting a method of use of the self-retaining screw inserter of FIG. 8. First a set screw 120 is placed on the distal tip 60, step 141. Then, the set screw 120 is secured or retained by engaging the threads 74 and 82, step 142. In this embodiment, the threads 74 and 82 are engaged by turning the knob 70 clockwise. Once the set screw 120 is retained, the set screw 120 may be placed in a desired location, step 143. Once the set screw 120 has been placed, the set screw 120 may be released by disengaging the threads 74 and 82, step 144. In this embodiment, the threads 74 and 82 may be disengaged by turning the knob 70 counter-clockwise. Using this method set screws may be both inserted and removed percutaneously. Other uses or implementations will be apparent to ones skilled in the art given the benefit of this disclosure.

Having the inner shaft 40 screw into the outer shaft 20 allows for constant and controlled active interference to be used to secure the set screw 120. Securing the set screw 120 in this manner is more durable and resistant to torque forces that may be applied by a user on the screw inserter. Another advantage is that the self retaining screw inserter 10 of the present invention can be disassembled into the component parts for easy cleaning.

Although, the previous examples have focused on a use of a threaded interface to engage and disengage the distal tip 60 with the push rod 50, other interfaces are possible. For example, ratchet, crank, or plunger interfaces may also be used. Other implementations and embodiments will be apparent to one skilled in the art given the benefit of this disclosure.

The present invention has been described relative to an illustrative embodiment. Since certain changes may be made in the above constructions without departing from the scope of the invention, it is intended that all matter contained in the above description or shown in the accompanying drawings be interpreted as illustrative and not in a limiting sense. For example, one skilled in the art will recognize that the instrument of the illustrative embodiment of the invention is not limited to use in percutaneous insertion and removal.

It is also to be understood that the following claims are to cover all generic and specific features of the invention described herein, and all statements of the scope of the invention which, as a matter of language, might be said to fall therebetween.

The invention claimed is:

1. A self-retaining screw inserter comprising:
an outer shaft defining an axially extending passageway;
an inner shaft comprising a push rod inserted into the axially extending passageway; and
an active reverse-collet retainer attached on an end of the outer shaft and comprising at least two fingers configured to retain a set screw, the active reverse-collet retainer defining a second passageway extending from the axially extending passageway,
wherein the push rod of the inner shaft moves in a first axial direction to engage the active reverse-collet retainer, and the push rod of the inner shaft moves in a second axial direction to disengage from the active reverse-collet retainer,
wherein a diameter of the second passageway is smaller than a diameter of the push rod so that the at least two fingers move radially outward to retain the set screw when the push rod of the inner shaft moves in the first axial direction to engage the active reverse-collet retainer, and the at least two fingers move radially inward to release the set screw when the push rod of the inner shaft moves in the second axial direction to disengage from the active reverse-collet retainer,
wherein a tip of the push rod that engages the active reverse-collet retainer is rounded to assist in the moving of the at least two fingers when the push rod of the inner shaft engages the active reverse-collet retainer.

2. The self-retaining screw inserter of claim 1 wherein the active reverse-collet retainer can be engaged from an end of the outer shaft opposite from the active reverse-collet retainer.

3. The self-retaining screw inserter of claim 2 wherein the active reverse collet retainer can be disengaged from the end of the outer shaft opposite from the active reverse-collet retainer.

4. A self-retaining screw inserter comprising:
an outer shaft defining an axially extending passageway, the outer shaft comprising:
a distal tip comprising at least two fingers configured to retain a set screw, and
a proximal end configured to receive an inner shaft; and
an inner shaft screwed into the outer shaft comprising a push rod configured to be inserted into the proximal end of the outer shaft and engage the distal tip of the outer shaft,
wherein the push rod of the inner shaft moves in a first axial direction to engage the distal tip of the outer shaft and the push rod of the inner shaft moves in a second axial direction to disengage from the distal tip of the outer shaft,
wherein the at least two fingers move radially outward to retain the set screw when the push rod of the inner shaft moves in the first axial direction and engages the distal tip by screwing the inner shaft in a first rotational direction, and the at least two fingers of the distal tip move radially inward to release the set screw when the push rod of the inner shaft moves in the second axial direction and disengages from the distal tip by turning the inner shaft in a second rotational direction,
wherein a tip of the push rod that engages the distal tip of the outer shaft is rounded to assist in the moving of the at least two fingers when the push rod of the inner shaft engages the distal tip of the outer shaft.

5. The self-retaining screw inserter of claim 4, wherein the outer and inner shafts are formed of stainless steel.

6. The self-retaining screw inserter of claim 4 wherein the inner shaft further comprises a knob on the proximal end of the push rod.

7. The self-retaining screw inserter of claim 6 wherein the proximal end of the outer shaft further comprises internal threads and the inner shaft further comprises threads configured to mate with the internal threads of the proximal end of the outer shaft.

8. The self-retaining screw inserter of claim 6 wherein engaging the threads of the proximal end of the outer shaft with the threads of the inner shaft causes the push rod to engage the distal tip of the outer shaft causing the two or more fingers of the distal tip to move radially outward allowing the distal tip to retain a set screw.

9. The self-retaining screw inserter of claim 8 wherein disengaging the threads of the proximal end of the outer shaft from the threads of the knob of the inner shaft causes the push rod to disengage the distal tip of the outer shaft causing the two or more fingers of the distal tip to move radially inward allowing the distal tip to release a set screw.

10. The self-retaining screw inserter of claim 4 wherein the outer shaft has scallops on an outer surface to reduce pressure when inserting and withdrawing the inserter percutaneously.

11. The self-retaining screw inserter of claim 4 wherein the outer shaft has surface configurations on an outer surface to assist in the manipulation of the screw inserter.

12. The self-retaining screw inserter of claim 4 wherein the fingers of the distal tip are shaped in a modified Torx head configuration.

13. A method of using a self retaining screw inserter comprising:
an outer shaft defining an axially extending passageway, the outer shaft comprising a distal tip comprising at least two fingers configured to retain a set screw, and a proximal end configured to receive an inner shaft; and
an inner shaft screwed into the outer shaft comprising a push rod configured to be inserted into the proximal end of the outer shaft and engage the distal tip of the outer shaft;
the method comprising:
placing a set screw on the distal tip of the outer shaft;
screwing the inner shaft in a first rotational direction to move the push rod of the inner shaft moves in a first axial direction;
retaining the set screw by screwing the inner shaft in the first rotational direction to engage the distal tip of the outer shaft with the push rod of the inner shaft, wherein when the push rod of the inner shaft engages the distal tip of the outer shaft, the at least two fingers of the distal tip move radially outward to retain the set screw;
screwing the inner shaft in a second rotational direction to move the push rod of the inner shaft in a second axial direction; and
releasing the set screw by screwing the inner shaft in the second rotational direction to disengage the push rod of the inner shaft from the distal tip of the outer shaft, wherein when the push rod of the inner shaft disengages from the distal tip of the outer shaft, the at least two fingers move radially inward tip to release the set screw,
wherein a tip of the push rod that engages the distal tip of the outer shaft is rounded to assist in the moving of the at least two fingers when the push rod of the inner shaft engages the distal tip of the outer shaft.

14. The method of claim 13 further comprising the step of placing the set screw in a desired location.

* * * * *